(12) United States Patent
Guo

(10) Patent No.: US 8,455,526 B2
(45) Date of Patent: *Jun. 4, 2013

(54) THERAPEUTIC USE OF IMIDAZOLE-5-CARBOXYLIC ACID DERIVATIVES

(75) Inventor: Jianhui Guo, Shanghai (CN)

(73) Assignee: Shanghai Allist Pharmaceuticals, Inc., Shanghai (CN)

( * ) Notice: Subject to any disclaimer, the term of this patent is extended or adjusted under 35 U.S.C. 154(b) by 138 days.

This patent is subject to a terminal disclaimer.

(21) Appl. No.: 12/663,183

(22) PCT Filed: Jun. 6, 2008

(86) PCT No.: PCT/CN2008/071213
§ 371 (c)(1),
(2), (4) Date: Mar. 5, 2010

(87) PCT Pub. No.: WO2008/148359
PCT Pub. Date: Dec. 11, 2008

(65) Prior Publication Data
US 2010/0168193 A1     Jul. 1, 2010

(30) Foreign Application Priority Data
Jun. 7, 2007   (CN) .......................... 2007 1 0093852

(51) Int. Cl.
*A01N 43/64* (2006.01)
*A61K 31/41* (2006.01)

(52) U.S. Cl.
USPC .......................................... 514/381; 514/387

(58) Field of Classification Search
USPC ................................................. 514/381, 382
See application file for complete search history.

(56) References Cited

U.S. PATENT DOCUMENTS

| 5,298,519 A | 3/1994 | Binder et al. | |
|---|---|---|---|
| 5,616,599 A | 4/1997 | Yanagisawa et al. | |
| 7,858,651 B2 * | 12/2010 | Guo et al. | 514/381 |
| 2009/0326024 A1 * | 12/2009 | Guo et al. | 514/381 |
| 2009/0326025 A1 * | 12/2009 | Lu et al. | 514/381 |
| 2010/0292286 A1 * | 11/2010 | Guo et al. | 514/381 |

FOREIGN PATENT DOCUMENTS

| CN | 1071426 A | | 4/1993 |
|---|---|---|---|
| CN | WO2007/095789 | * | 8/2007 |
| EP | 0535420 A1 | | 4/1993 |
| EP | 1988090 A1 | | 11/2008 |
| EP | 2116242 A1 | | 11/2009 |
| WO | WO-2005/011646 A2 | | 2/2005 |
| WO | WO-2005/023182 A2 | | 3/2005 |
| WO | WO-2007/095789 A1 | | 8/2007 |

OTHER PUBLICATIONS

Wolfgang Wienen, et al, A review on Telmisartan: A Novel, Long-acting Angiotensin II-Receptor Antagonist, 18 Cardio. Drug Rev. 127 (2000).*
Machine Translation of Foreign Priority Application CN200710093852.X.*
Ma, et al., "Effects of Losartan on Cardiac and Renal Functions in Elderly Hypertensive Patients", Journal of Jilin University (Medicine Edition), vol. 31, 2005, pp. 620-622.
Wolf, S., et al., *Sind alle Antihypertensiva nephroprotektiv?* (2004), Herz 29, Nr. 3, pp. 248-254.
Dahlöf, B., *End-Organ Damage: does it really matter how we prevent it?* (2003), European Heart Journal Supplements 5 (Supplement F), pp. F33-F39.
Grandi, A.M., et al., *Blockade of the renin-angiotensin-aldosterone system: Effects on hypertensive target organ damage* (2006), vol. 4, Cardiovascular and Hematological Agents in Medicinal Chemistry, pp. 219-228.

* cited by examiner

*Primary Examiner* — Sean Basquill
(74) *Attorney, Agent, or Firm* — Connolly Bove Lodge & Hutz LLP

(57) ABSTRACT

The invention discloses the use of 2-butyl-4-chloro-1-[2'-(1H-tetrazol-5-yl)1,1'-biphenyl-methyl]-imidazole-5-carboxylic acid, 1-[(isopropoxycarbonyl)oxy] methyl ester and the pharmaceutically acceptable salts thereof in the manufacture of a medicament for the treatment of the damage of a target organ caused by hypertension. It particularly discloses the use of this compound in the manufacture of a medicament for the treatment of left ventricular hypertrophy, renal dysfunction, aorta thickening caused by hypertension, which provides an effective drug and method for the treatment of the damage of target organs for hypertension patients.

12 Claims, 2 Drawing Sheets

THERAPEUTIC USE OF IMIDAZOLE-5-CARBOXYLIC ACID DERIVATIVES

RELATED APPLICATIONS

This application is a national stage application (under 35 U.S.C. §371) of PCT/CN2008/071213, filed Jun. 6, 2008, which claims benefit of People's Republic of China application 200710093852.X, filed Jun. 7, 2007.

TECHNICAL FIELD

The invention relates to the use of 2-butyl-4-chloro-1-[2'-(1H-tetrazol-5-yl)1,1'-biphenyl-methyl]-imidazole-5-carboxylic acid, 1-[(isopropoxycarbonyl)oxy] methyl ester and a pharmaceutically acceptable salt thereof in the manufacture of a medicament for the treatment of the damage of a target organ caused by hypertension. In particular, it relates to the use of this compound and the composition thereof in the manufacture of a medicament for the treatment of the damage of heart, brain, kidney or blood vessel caused by hypertension. The invention provides effective medicaments and methods for the treatment of the damage of target organs for hypertension patients.

BACKGROUND OF THE INVENTION

Hypertension is one of the commonest cardiovascular diseases. The main manifestation of its clinical syndrome is elevation of arterial blood pressure in systemic circulation. The two main types of hypertension are primary and secondary hypertension. The majority is primary hypertension. More than 95 percent of hypertensive patients suffer from it. As the development of social economy, improvement of life level of the people, and the prolongation of lifetime of human, the prevalence of hypertension shows a trend of continuously elevation. As estimated, 18.8 percent of adults in China suffer from hypertension, and there are 0.16 billion hypertensive patients in the whole country. In this population of hypertensive patients, awareness rate of hypertension is 30.2 percent, treatment rate is 24.7 percent, and control rate is 6.1 percent, which are all in worse level.

If hypertension is not controlled and treated effectively, it will cause coronary arteriosclerosis, coronary heart disease, angina pectoris, and even very serious complication, such as hypertensive heart disease and heart failure. In addition, long-term hypertension will result in renal dysfunction, which makes patients incapacitated, even losing their lives. The recently published result of eight-year follow-up survey of 170 thousand people in China, all over 40 years old, showed that cardiovascular disease is already the first cause of death in China, and hypertension is one of the major risk factors. The burden brought from hypertension and its related diseases is so heavy. An estimation of 300 billion RMB is expensed by cardiovascular diseases each year in China.

Drug treatment is one of the major therapies to control hypertension effectively. In the therapeutic field of antihypertensive drugs, common antihypertensive drugs include the types as follows: 1) diuretics, which act by increasing the excretion by the kidneys of sodium in the urine to aid the elimination of sodium and water from the body, and lower blood pressure by reducing blood volume. As a basic agent, diuretics are used to treat mild and moderate hypertension, especially suitable for aged or hypertensive patients combined with heart failure. The main side effects associated with diuretics is an increased elimination of potassium, resulting in a low level of potassium in the body, which increases the risk of heart rhythm disturbances that can be serious, and also hinders antihypertensive effect of diuretics. 2) β receptor blockers, which produce antihypertensive effects by many kinds of action pathways, including several aspects as follows: (1)reduction in cardiac output to make the body produce adaptive response, thus reduces the peripheral vascular resistance and lowers the blood pressure; (2) blockade of β receptor in central nervous system to decrease neural conduction of sympathetic fibers; (3) blockade of the excitatory receptor of presynaptic membrane β2 to decrease the release of NE; (4) inhibition of the release of renin; (5) increasing the vasodilative effect of ANP and PGI2; (6) rebuilding pressure receptor and so on. The adverse effects of β receptor blockers include the following: fatigue, limb cold, gut discomfort, eye scintillation, blind spot and so on. 3) α1 receptor blockers, which dilate resistance vessels and capacitance vessels by selective action on the synaptic α1 receptor and thus decrease arterial blood pressure. α1 receptor blockers have significant antihypertensive effect, which also can decrease plasma cholesterol and triglyceride concentration, improve insulin resistance, and slightly reverse LVH. With inhibitive effect on prostate, they can significantly improve dysuria for the patients of prostatic hyperplasia. α1 receptor blockers are applicable for the patients with glucose or lipid metabolic abnormality or prostatic hyperplasia. The adverse effects of these agents are headache, dizziness, palpitation, asthenia and so on. Their disadvantages are the appearance of peripheral edema, weight gain, and the first dose phenomenon i.e., postural hypotension. 4) $Ca^{++}$ antagonists, which selectively block the influx of $Ca^{++}$ in the specific L type calcium channel on the membrane of vascular smooth muscle and myocardium to relax vascular smooth muscle and reduce the vascular resistance. The main adverse effects of $Ca^{++}$ antagonists are flush face (particularly seen in short-effect dihydropyridines), headache, dizziness, palpitation, constipation and ankle edema, which are related to vascular excessive vasodilatation. The adverse effects can be alleviated by using small dosage at the beginning. 5) ACE inhibitors, which act on renin-angiotensin-aldosterone system (RAS). These agents bind with Angiotensin I converting enzyme to inhibit Angiotensin II formation, and make the decomposition of bradykinin slow, which result in vasodilatation and decline of blood pressure. The common main adverse effects of ACEI are dry cough and angioneurotic edema. If replenishers with potassium together with diuretics retaining potassium are taken simultaneously, hyperkalemia will easily appear.

Angiotensin II receptor blacker (ARB) is a new type of antihypertensive agents acting on renin-angiotensin-aldosterone system (RAS) after ACEI. ABR acts on the terminal position of RAS, which can play highly efficient role to block the binding of Angiotensin II (Ang II) with its receptor, so that achieve the functions of dilating blood vessels and reducing blood pressure. In 1994, the first (AT1) antagonist, losartan potassium was marketed by Merck Company (US). Because of its good efficacy, many pharmaceutical companies all over the world devoted into this field. The same type of products such as valsartan (Novartis), irbesartan (Sanofi Aventis), candesartan (Takeda), eprosartan (Smiklane Beecham), telmisartan (Boehringer Ingelheim), olmesartan (Sankyo), were marketed subsequently. The antihypertensive efficacy of sartan-class drugs is similar to ACEI and $Ca^{++}$ antagonists. However, ARB-class drugs have more tolerance, fewer side effects and fewer common adverse effects such as causing cough and edema, so that are safer drugs to treat hypertension. As the tangible efficacy from the special mechanism of ARB-class drugs, they have become the mainstream drugs in antihypertensive market.

Nevertheless, the antihypertensive treatment is long-term, even life-long, which need to have the characteristics of low toxicity and protection of vital target organs, as well as tangible efficacy. The antihypertensive drugs mentioned above do not meet the above requirement. Therefore, there is an urgent need to continually develop novel antihypertensive drugs with high efficiency, low toxicity and the function of protecting vital target organs.

SUMMARY OF THE INVENTION

The purpose of the invention is to provide a novel antihypertensive drug with high efficiency, low toxicity and the function of protecting vital target organs.

In the first aspect, the present invention provides the use of a compound of formula I, or a pharmaceutically acceptable salt thereof in the manufacture of a medicament for the treatment of the damage of a target organ caused by hypertension

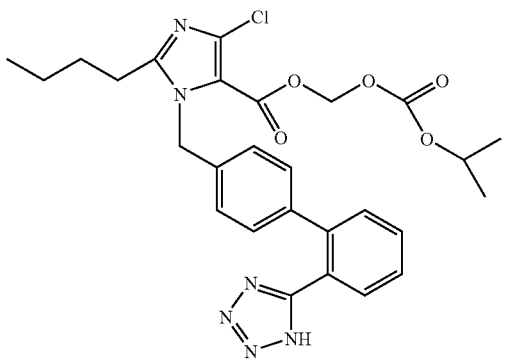

(I)

In another preferred embodiment of the present invention, said damage of a target organ comprises the damage of heart, brain, kidney or blood vessel.

In another preferred embodiment of the present invention, said damage of a target organ comprises left ventricular hypertrophy, stroke, renal cortex atrophy or aorta thickening.

In another preferred embodiment of the present invention, said medicament comprises 20 mg-1000 mg (preferably 50-500 mg) of the compound of formula (I) or a pharmaceutically acceptable salt thereof, and a pharmaceutically acceptable carrier.

In another preferred embodiment of the present invention, the content of the compound of formula (I) or the pharmaceutically acceptable salt thereof in said medicament is 100 mg, 200 mg, 300 mg, 400 mg, 500 mg, 600 mg, 700 mg, 800 mg, 900 mg or 1000 mg.

In another preferred embodiment of the present invention, the dosage form of said medicament is oral dosage form, injection, formulation for sublingual administration, or patch. The oral dosage form preferably comprises tablet, capsule, granule, pill, or suspension.

In the second aspect, the present invention provides the use of a composition comprising the compound of formula (I) or a pharmaceutically acceptable salt thereof in the manufacture of a medicament for the treatment of the damage of a target organ caused by hypertension

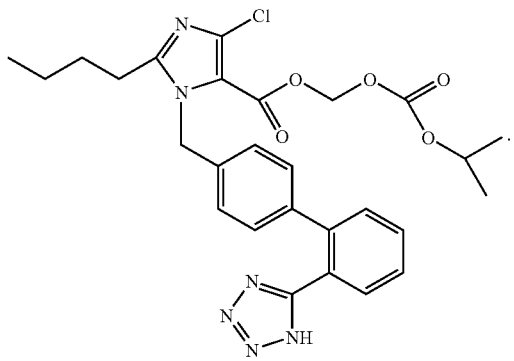

(I)

In another preferred embodiment of the present invention, the content of the compound of formula (I) or the pharmaceutically acceptable salt thereof in the composition is 20 mg-1000 mg.

In the third aspect, the present invention provides a pharmaceutical composition for oral or sublingual administration, which contains 50 mg-1000 mg of a compound of formula (I) or a pharmaceutically acceptable salt thereof and a pharmaceutically acceptable carrier

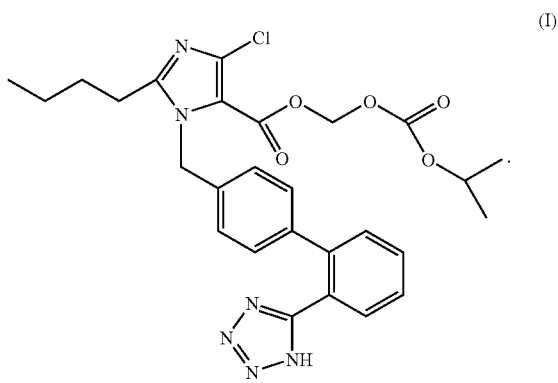 [SMILES: CCCCc1nc(Cl)c(C(=O)OCOC(=O)OC(C)C)n1Cc1ccc(-c2ccccc2-c2nnn[nH]2)cc1]

(I)

In the fourth aspect, the present invention provides a method for the treatment of the damage of a target organ caused by hypertension, comprising administering to a subject in need thereof a compound of formula (I) or a pharmaceutically acceptable salt thereof in the dosage of 0.5-50 mg/kg/day (preferably 1-20 mg/kg/day, more preferably >2 mg/kg/day or >3 mg/kg/day).

In the fifth aspect, the present invention provides a pharmaceutical composition for the treatment of the damage of a target organ caused by hypertension, comprising (a) a pharmaceutically acceptable carrier, and (b) a compound of formula (I) or a pharmaceutically acceptable salt thereof.

CONTENTS OF THE INVENTION

Figure 1:
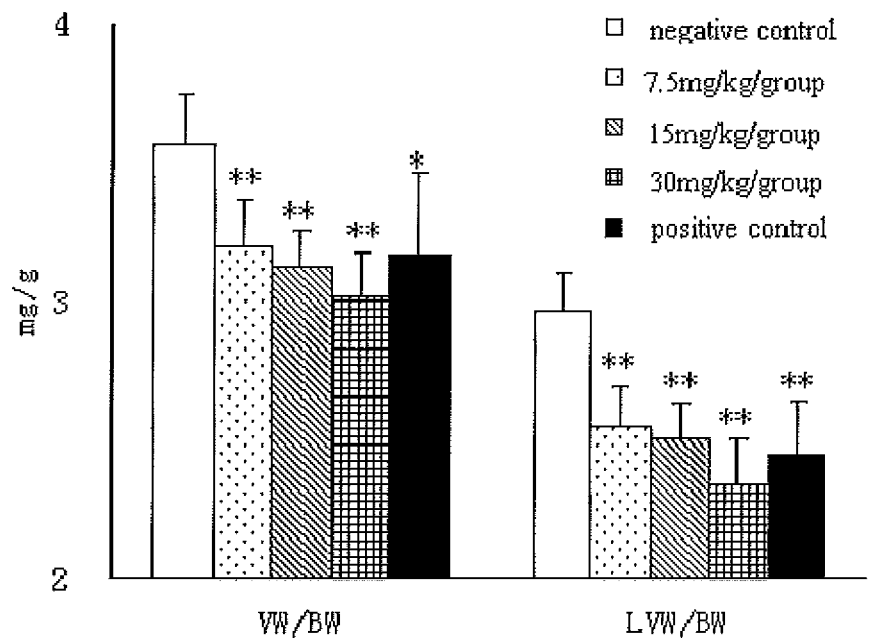
FIG. 1—Heart Protection—Allisartan has reversing effect on left ventricular hypertrophy of SHR.

The inventor has researched extensively and discovered that the compound of formula (I) or the pharmaceutically acceptable salts thereof (Allisartan and the salts thereof) have a significant function of alleviating the damage of target organs caused by hypertension while playing a role of reducing blood pressure. Allisartan has few toxicity and good safety. It can be used in animal and human body with high dosage. The present invention is obtained on this basis to provide a kind of efficient drugs and a method to treat the damage of target organs for hypertensive patients In the present invention, the term "the compound of the present invention" used herein means the compound of formula (I) or the pharmaceutically acceptable salts thereof. PCT/CN2006/001914 of the present applicant firstly discloses a series of imidazole-5-carboxylic acid derivatives. The characteristic of the structure thereof is 5-gem-diacid ester group in the imidazole ring. In particular, PCT/CN2006/001914 discloses the compound, 2-butyl-4-chloro-1-[2'-(1H-tetrazol-5-yl)1,1'-biphenyl-methyl]imidazole-5-carboxylic acid, 1-[(isopropoxycarbonyl)oxy]methyl Ester, which is abbreviated as Allisartan in the present invention. The chemical structure thereof is as follows:

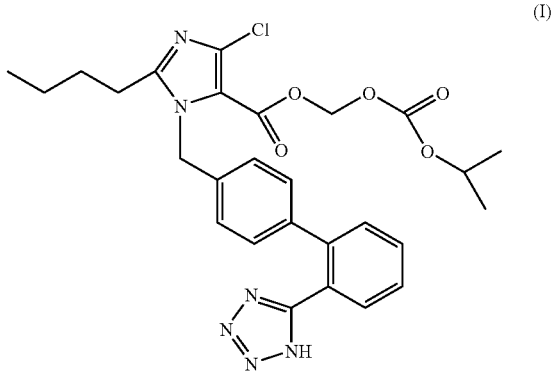 [SMILES: CCCCc1nc(Cl)c(C(=O)OCOC(=O)OC(C)C)n1Cc1ccc(-c2ccccc2-c2nnn[nH]2)cc1]

(I)

In the present invention, the term "pharmaceutically acceptable salt" means relatively non-toxic inorganic acid or basic addition salts or organic acid or basic addition salts of the compound of formula (I). These salts may be prepared in situ during the final isolation and purification of the compounds; alternatively, prepared by reacting the purified compounds in a form of free alkali with appropriate organic or inorganic acids and separating the salts. Representative salts include hydrobromide, hydrochloride, sulfate, maleate, fumarate, succinate and the like. They also include salts comprising cations, such as salts of alkali metals and alkali-earth metals, such as sodium, lithium, potassium, calcium, magnesium, quaternary ammonium and ammonium cation salts. Particularly preferred salts are alkali metal cation salts and alkali earth metal salts.

The study of the inventor showed that Allisartan exhibits strong antihypertensive activity in animals. Compared with other Ang II receptor antagonists, this compound has the advantage of low toxicity, and thus is suitable to be developed as an ideal antihypertensive drug.

Therefore, the present invention first discloses use of 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester in the manufacture of a medicament for the treatment of the damage of a target organ caused by hypertension.

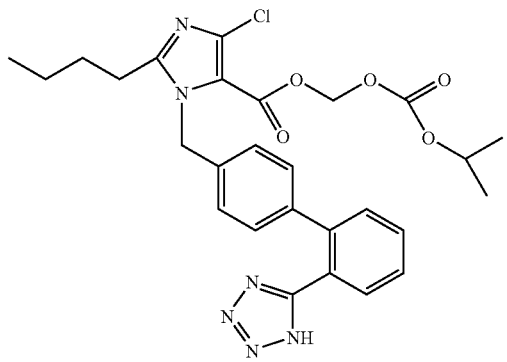 [SMILES: CCCCc1nc(Cl)c(C(=O)OCOC(=O)OC(C)C)n1Cc1ccc(-c2ccccc2-c2nnn[nH]2)cc1]

The damage of a target organ includes the damage of heart, brain, kidney and blood vessel and the like caused by sustained high blood pressure. The specific manifestations include left ventricular hypertrophy, dilation, and congestive heart failure caused by hypertension; coronary atherosclerosis, angina pectoris, myocardial infarction, heart failure and sudden death caused by hypertension; microaneurysm, brain artery thrombosis caused by long-term hypertension; renal artery atherosclerosis, nephrosclerosis, proteinuria, renal dysfunction, renal failure and the like caused by sustained high blood pressure. In the present invention, Allisartan has good efficacy to alleviate left ventricular hypertrophy, renal dysfunction, aortic thickening caused by hypertension.

Meanwhile, the present invention discloses use of a composition comprising 2-butyl-4-chloro-1-[2'-(1H-tetrazol-5-yl)1,1'-biphenyl-methyl]imidazole-5-carboxylic acid, 1-[(isopropoxycarbonyl)oxy]methyl ester, in the manufacture of a medicament for the treatment of the damage of a target organ caused by hypertension.

As known by the skilled in the art, the medicament containing allisartan can be manufactured by the method of addition the pharmaceutical acceptable carriers to treat the damage of a target organ caused by hypertension. Allisartan may be mixed with at least one conventional inert excipients (or carriers) such as citrate sodium, dicalcium phosphate, or with the following components: (a) fillers or bulking agents, for example, starch, lactose, sucrose, glucose, mannitol and silicic acid; (b) binders, for example, hydroxymethylcellulose, alginate, gelatin, polyvinylpyrrolidone, sucrose, and arabic gum; (c) humectants, for example, glycerin; (d) disintegrants, for example, agar, calcium carbonate, potato starch or cassava starch, alginic acid, some composite silicate and sodium carbonate; (e) slow-dissolving agents, for example, wax, (f) sorbefacients, for example, quaternary ammonium compound; (g) wetting agents, for example, cetyl alcohol and glycerin monostearate; (h) adsorbents, for example, kaolin; and (i) lubricants, for example, talc, calcium stearate, magnesium stearate, solid polyethylene glycol, sodium dodecyl sulfate or mixture thereof.

The medicament containing Allisartan can be manufactured in the forms of granules, tablets and capsules by conventional methods, such as mixing, granulating, tabletting, and encapsulating. If the selected filler or disintegrant are sensitive to water, the waterproof film coat material may be selected to coat by conventional methods in pharmaceutical practice. Or sugar-coat may be selected to meet the requirement of better taste by conventional methods in pharmaceutical practice. The skilled in the art can obtain reasonable formulation proportion and preparation method by simple prescription and technological screening.

Allisartan can be manufactured as liquid dosage forms, which may include pharmaceutically acceptable emulsions, solutions, suspensions, syrups or tinctures. Beside the active compound, the liquid dosage form may include inert diluents conventionally used in this field, such as water or other solvents, solubilizing agents and emulsifying agents, such as ethanol, isopropanol, ethyl carbonate, ethyl acetate, propylene glycol, 1,3-butanediol, dimethylformamide and oil, particularly cottonseed oil, peanut oil, corn germ oil, olive oil, caster oil and sesame oil or the mixture thereof. Beside the inert diluents, the composition may also include auxiliary agents such as wetting agents, emulsifying agents and suspending agents, sweetening agents, flavouring agents and flavors. Beside the active compound, the suspension may include suspending agents, for example, ethoxylated isooctadecanol, polyoxyethylene sorbitol, and polysorbates, microcrystalline cellulose, methanol aluminum and agar or the mixture thereof.

In the process of the preparation of the medicament containing Allisartan, Allisartan is dispersed in the pharmaceutical acceptable carrier first to make the compound disperse in the carrier material in molecular, colloidal, microcrystalline or amorphous state, so that to achieve the same purpose as micronization, which can obtain higher dispersion and increase dissolution of the compound. There are three main types of carriers, water-soluble, insoluble and intestine soluble, which are called solubilization carriers. The carriers can be selected from polyethylene glycols, povidones, surface surfactants containing polyoxyethylene group, water soluble cellulose derivatives, organic acids, sugars and alcohols. These kinds of carriers can be used alone or combined to obtain the form with good dispersion.

In the process of the present invention, the MTD value of Allisartan in single gavage to mice>10 g/kg; the MTD value of Allisartan in single oral administration to Beagle>2500 mg/kg; the body weight, the amount of eaten food, hematology, blood biochemical analysis and pathology are normal after the long-term administration of Allisartan with the dosage of 320 mg/kg/day for rats and the long-term administration of Allisartan with the dosage of 500 mg/kg/day for Beagle dogs, which showed that high dosage of Allisartan is safe. Therefore, in the process of the manufacture of a medicament containing Allisartan, the unit dosage can be lower or higher, such as 20 mg-1000 mg, specifically 20 mg, 50 mg, 100 mg, 200 mg, 300 mg, 400 mg, 500 mg or 1000 mg. Preferably, the unit dosage of Allisartan is higher, such as 100 mg, 200 mg, 300 mg, 400 mg, 500 mg or 1000 mg, to give the form which can efficiently alleviate the damage of target organs caused by hypertension.

The medicament containing Allisartan prepared above can be directly administered to people. The mode of administration can be oral or sublingual. It can be administered alone or combined with other pharmaceutically acceptable compounds.

In another aspect, the present invention also provides a method for the treatment of the damage of a target organ, such as heart, brain, kidney, blood vessel and the like, caused by hypertension, particularly for the treatment of left ventricular hypertrophy, renal cortex atrophy or aortic thickening, comprising administering an Allisartan containing medicament to the human body. The dosage of Allisartan given to the human body is 0.1-50 mg/kg/day, preferably 0.5-20 mg/kg/day. Specifically, the dosage can be 20 mg-1000 mg/day, such as 20 mg, 50 mg, 100 mg, 200 mg, 300 mg, 400 mg, 500 mg or 1000 mg per day. Preferably, the dosage of Allisartan administered per day is higher, such as 100 mg, 200 mg, 300 mg, 400 mg, 500 mg or 1000 mg, to obtain good effect to treat of the damage of a target organ caused by hypertension.

By the present invention, Allisartan can not only be used for the treatment of hypertension, but also can be used in the field of developing new therapeutics to obtain a kind of efficient drugs and methods to treat the damage of the target organs caused by hypertension.

The main advantages of the present invention are listed as follows:

(1) The compound of the present invention has high lipid solubility, which makes it easily penetrate into tissues and cells to play its role.

(2) The compound of the present invention has quite low toxicity and good safety. The maximum tolerated dosages of several sartan drugs reported in literatures are Valsartan 320 mg/d, Losartan 100 mg/d, Olmesartan 40 mg/d. The results of phase I clinical trial of Allisartan indicated that it is very safe for healthy subjects to take Allisartan (20-400 mg) by single oral administration, and there are no adverse events or serious adverse events.

(3) The compound in the present invention has significant efficiency against many kinds of damages of target organs caused by hypertension.

Taken in conjunction with the following examples, the invention will be described in detail. It should be understood that the examples are illustrative only and will not intend to limit the scope of the invention. Unless otherwise indicated, the amounts and percents are by weight.

EXAMPLES

Evaluating Methods for Pharmacological Effect of Alleviating Damages of Target Organs Caused by Hypertension:

Spontaneous hypertensive rat (SHR) was administered successively, then anesthetized by intraperitoneal injection with 5 mg/kg of diazepam and 50 mg/kg of hydrochloride chlorine ammonia ketone. Then it was supined and fixed on the mice plate. The blood pressure was measured by inserting self-made artery catheter from left femoral to low positioned abdominal aorta. Left femoral vein intubation was used in intravenous administration, and then gastric fistula intubation was used. The gastric tube, artery catheter and vein catheter were passed under skin of the back to export from the neck incision. After the surgery, the animal was recovered for 40-45 h in bright automatic switching animal room with constant temperature and humidity. The recovered animal was connected in the monitoring device for measuring the blood pressure of rat with conscious free activity, and was stabilized for 3-4 h. The artery catheter was connected with pressure transformer by the perfusion tee tube. Systolic pressure per pulse, diastolic blood pressure and interphase of heart moving were real-time recorded by a computer. The systolic blood pressure (SBP), diastolic blood pressure (DBP) and heart interphase (HP) were recorded successively for 4 h. Phenylephrine was injected in femoral vein after the recording of blood pressure. The arterial baroreflex sensitivity (BRS) was measured twice and mean value was taken. The animal was sacrificed by decapitating method after recording the hemodynamic parameters and measuring the BRS. The thoracic cavity and abdominal cavity of the rat were opened, and the heart, thoracic aorta and right kidney were took quickly into normal saline. The large blood vessels of the base of the heart were removed and the whole heart was weighed after the water was completely absorbed by filter paper. The left and right ventricles were isolated and weighed respectively after the water was completely absorbed by filter paper. The right kidney was weighed after the water was completely absorbed. Then, the fat tissue and connective tissue adhered on the thoracic aorta were removed. The aortic arch was cut from the distal branch of subclavian artery to obtain a segment of the thoracic aorta of 3 cm, and weighed after the water was completely absorbed by filter paper.

Evaluation indexes: LVW/BW, RVW/BW and VW/BW are the ratios of the left ventricle weight, right ventricle weight, ventricle weight to the body weight, respectively. They reflect the degree of heart damage. A lower ratio means weak damage. RKW/BW is the ratio of right kidney weight to body weight, which reflects the degree of the renal damage. A higher ratio means weak damage. AW/LH (length) is the ratio of aorta weight to length, which reflects the degree of the aorta damage. A lower ratio means weak damage.

Example 1

The Preparation of 2-butyl-4-chloro-1-[2'-(1H-tetrazol-5-yl)-1,1'-biphenyl-methyl]-imidazole-5-carboxylic acid, 1-[(isopropoxycarbonyl)oxy]methyl ester (Allisartan)

2-butyl-4-chloro-1-[2'-(1H-tetrazol-5-yl)1,1'-biphenyl-methyl]-imidazole-5-carbo-xylic acid (prepared by the method disclosed in U.S. Pat. No. 5,138,069) was reacted with trityl chloride to obtain 2-butyl-4-chloro-1-[2'-(1-trityl-tetrazol-5-yl)1,1'-biphenyl-methyl]-imidazole-5-carboxylic acid. To a 100 ml-one-necked flask, 0.523 g of 2-butyl-4-chloro-1-[2'-(1-trityl-tetrazol-5-yl)1,1'-biphenyl-methyl]-imidazole-5-carboxylic acid, 0.124 g of potassium carbonate, 5 ml of N,N-dimethylacetamide were added in turn. The solution was stirred at room temperature for 20 minutes. Then 0.562 g of 1-chloromethyl isopropyl carbonate was added and the mixture was reacted at 45-50□ for 16 hours. After the reaction was completed, the mixture solution was filtered, and 30 ml of water was added into the filtrate. The resulting mixture was extracted with 30 ml of ethyl acetate twice. The organic phase was dried and concentrated to give 1.724 g of oil, which was directly used in the next reaction without purification.

10 ml of dioxane and 5 ml of HCl (4 mol/L) were added, and the resulting mixture was reacted at room temperature for 16 hours. The reaction was stopped and the solution was adjusted to pH 6-7 using aqueous sodium bicarbonate solution. The solution went turbid, and was extracted with ethyl acetate. The organic phase was washed with saturated brine, dried, concentrated to give 0.436 g of 2-butyl-4-chloro-1-[2'-(1H-tetrazol-5-yl)1,1'-biphenyl-methyl]-imidazole-5-carboxylic acid, 1-[(isopropoxycarbonyl)oxy]methyl ester.

1H-NMR (CDCl3) δ H (ppm): 0.89 (t, 3H, J=14.6), 1.24 (d, 6H, J=6.3), 1.37 (m, 2H, J=22.1), 1.69 (m, 2H, J=30.5), 2.64 (t, 2H, J=15.5), 4.81 (m, 1H, J=12.4), 5.54 (s, 2H), 5.86 (s, 2H), 6.95-7.64 (8H), 8.08 (d, 1H, J=7.42)

ESI (+) m/z: 552.7

Mp: 134.5-136□

The preparation of 2-butyl-4-chloro-1-[2'-(1H-tetrazol-5-yl)1,1'-biphenyl-methyl]-imidazole-5-carboxylic acid, 1-[(isopropoxy-carbonyl)oxy]methyl ester potassium salt (Allisartan potassium)

To a 100 ml-three-necked flask, 2.50 g (4.52 mmol) of 2-butyl-4-chloro-1-[2'-(1H-tetrazol-5-yl)1,1'-biphenyl-methyl]imidazole-5-carboxylic acid, 1-[(isopropoxy-carbonyl)oxy]methyl ester, and 25 ml of tetrahydrofuran (THF) were added. The solution was stirred, and 0.645 g (4.52 mmol, 90% contents Aldrich Company) of trimethyl silanol potassium in 15 ml of THF was added and the mixture was reacted at room temperature (28 C) for 17 h.

After reaction, a little of white floccule was precipitated in the reaction solution, filtered and the filtrate was concentrated in vacuum to obtain white solid crude product, which was recrystallized by the mixture solution of isopropyl ether and ethanol (3:1 v/v) to give 1.42 g of 2-butyl-4-chloro-1-[2'-(1H-tetrazol-5-yl)1,1'-biphenyl-methyl]-imidazole-5-carboxylic acid, 1-[(isopropoxy-carbonyl)oxy]methyl ester potassium salt with yield of 53%.

Mp: 189.5-189.7 C.

Example 2

The Protection Effect of Allisartan and its Potassium Salts to the Target Organs of Hypertensive Rats.

Spontaneous hypertensive rats (SHR) were randomly divided into 5 groups, which include negative control group (fed on normal rat materials), positive control group (losartan potassium 30 mg/kg), low dosage Allisartan group (7.5 mg/kg), middle dosage Allisartan group (15 mg/kg) and high dosage Allisartan group (30 mg/kg). After the rats were fed on four specs of rat feed for four months, the SBP, DBP and HP were real-time recorded for 4 h. The animal was sacrificed by decapitating method. The thoracic cavity and abdominal cavity of the rat were opened, and the heart, thoracic aorta and right kidney were took quickly into normal saline. The large blood vessels of the base of the heart were removed and the whole heart was weighed after the water was completely adsorbed by filter paper. The left and right ventricles were isolated and weighed respectively after the water was completely absorbed by filter paper. The right kidney was weighed after the water was completely absorbed. Then, the fat tissue and connective tissue adhered on the thoracic aorta were removed. The aortic arch was cut from the distal branch of subclavian artery to obtain a segment of the thoracic aorta of 3 cm, and weighed after the water was completely absorbed by filter paper. The indexes of general observation for terminal organ damages were analyzed. The experimental data were summarized in table 1 and table 2.

TABLE 1

The effects of Allisartan on the blood pressure and heart rate of SHR

| group | n | SBP(mmHg) | DBP(mmHg) | HP(ms) |
|---|---|---|---|---|
| Negative control | 12 | 175 ± 13.67 | 122 ± 16.11 | 172 ± 14.75 |
| Low dosage group | 11 | 141 ± 9.44*** | 100 ± 5.98*** | 176 ± 9.65 |
| Middle dosage group | 11 | 132 ± 8.35*** | 90 ± 5.74*** | 179 ± 10.83 |
| High dosage group | 9 | 121 ± 10.25*** | 81 ± 6.20*** | 184 ± 16.62 |
| Positive control | 11 | 124 ± 12.96*** | 84 ± 9.56*** | 187 ± 11.95 |

***$P < 0.001$ vs negative control group

TABLE 2

The indexes of general observation for organ damages

| group | VW/BW(mg/g) | LVW/BW(mg/g) | RKW/BW(mg/g) | AW/LH(mg/cm) |
|---|---|---|---|---|
| Negative control | 3.57 ± 0.18 | 2.97 ± 0.14 | 3.90 ± 0.11 | 11.94 ± 0.99 |
| Low dosage group | 3.20 ± 0.16** | 2.55 ± 0.15*** | 4.00 ± 0.3 | 10.52 ± 0.6** |
| Middle dosage group | 3.13 ± 0.13*** | 2.51 ± 0.13*** | 4.24 ± 0.34** | 9.60 ± 0.81*** |
| High dosage group | 3.01 ± 0.17*** | 2.34 ± 0.16*** | 4.24 ± 0.13*** | 9.26 ± 0.68*** |
| Positive control | 3.18 ± 0.29 | 2.45 ± 0.2*** | 4.00 ± 0.23 | 9.07 ± 0.65*** |

**P < 0.01
***P < 0.001 vs negative control group

Except for antihypertensive effect, Allisartan also has protection effect on target organs:

Heart Protection

Compared with ventricular weight in negative control group, the ventricular weights in three groups with low, middle and high dosages of Allisartan are all significantly lower, among which, the reductions in ventricular weight/body weight and left ventricular weight/body weight are more significant (P<0.001). It indicates that Allisartan has reversing effect on left ventricular hypertrophy of SHR. See FIG. 1.

Right Kidney Protection

Figure 2:
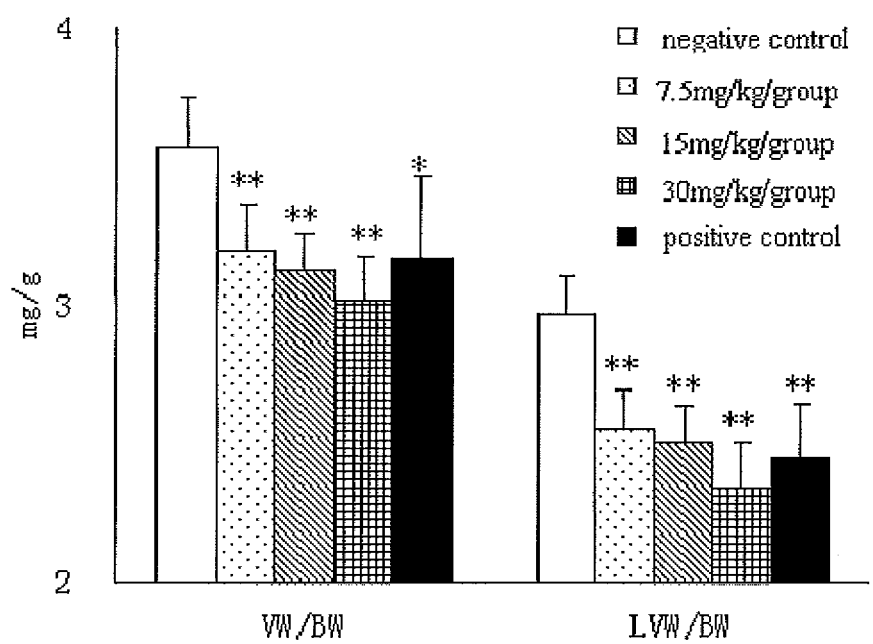
FIG. 2—Right Kidney Protection—Allisartan has good effect against renal cortex atrophy.

Compared with negative control group, the right kidney weights of three groups with low, middle and high dosages of Allisartan and positive control group are all significantly higher, among which, the effects on the groups of middle and high dosages are more significant. It indicates that Allisartan has good effect against renal cortex atrophy. See FIG. 2.

Aorta Protection

Figure 3:
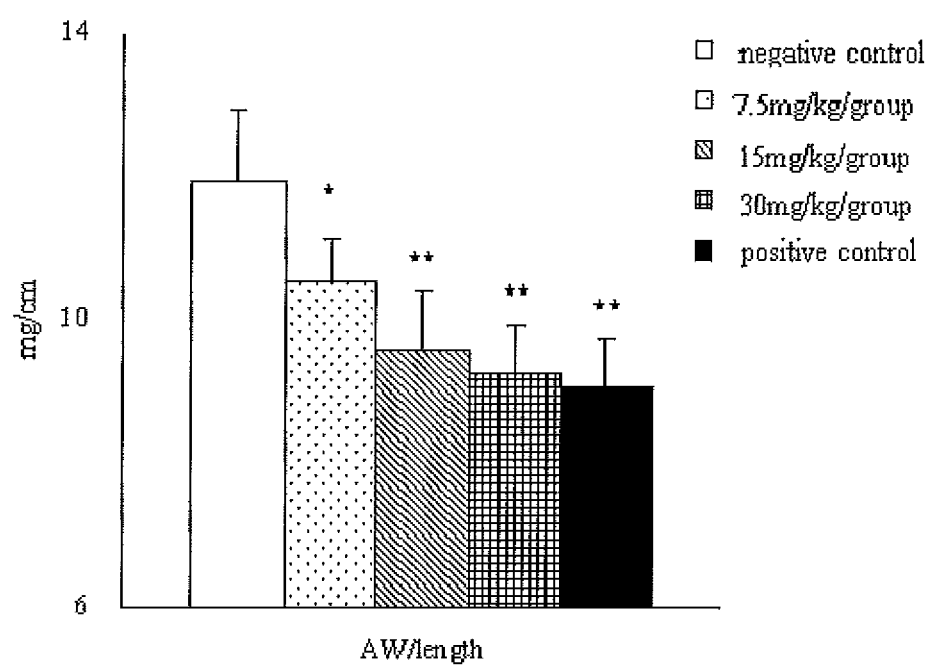
FIG. 3—Aorta Protection—Allisartan has good effect against aorta thickening.

Compared with negative control group, the unit aorta weights of three groups with low, middle and high dosages of Allisartan and positive control group are all significantly lower, among which, P<0.01 in the group with low dosage, P<0.001 in the groups with middle and high dosages. It indicates that Allisartan has good effect against aorta thickening. See FIG. 3.

After the spontaneous hypertensive rats (SHR) were administered with Allisartan potassium, the results proved that the protective effect of Allisartan potassium against damages of target organs is similar to that of Allisartan.

Example 3

The Safety of High Dosage of Allisartan
1. Maximum Tolerance Dose of Allisartan by Single Gavage Tested in Mice 40 ICR mice were randomly divided into 2 groups, 20/group, and half male and half female. There were a group of the dosage of 10 g/kg Allisartan and a solvent control group. Instantaneous response was observed after administration by single gavage. After observed successively for 14 days, the toxic reaction and death were recorded. Compared with the control group, except that the weight gain of the male mice were slower from the second day to the ninth day after administration in the drug group, there was no drug related change in terms of appearance, behavior, the response to stimulation, secretion and excreta in the male and female mice. No mouse was dead. All mice were dissected on the fifteenth day. There is no visual abnormal in heart, liver, spleen, lung, kidney, stomach, intestine, thymus, ovary, testis and the like, which proved that the MTD value>10 g/kg when single gavage of Allisartan to mice.

2. Acute Toxicity Test of Beagle Dog by Single Oral Administration of Allisartan 2 Beagle dogs were about six-month old with the weight of 7 kg each, 1 male and 1 female. The dosage of Allisartan by single oral administration was 2500 mg/kg. After being observed for 14 days after administration, feeding and feces were normal for Beagle dogs, and there were no significant changes in weight, cardiac electricity, blood and biochemistry. The result of histopathology examination showed that there was no drug correlated lesions in heart, lung, liver, spleen, kidney and the like, which proved that the MTD value>2500 mg/kg when single gavage of Allisartan to beagle dogs.

3. Safety of Long-Term Administration to Rats

SD rats were administered by gavage with Allisartan for 26 weeks, and they were observed for six weeks during the recovery period. There were three groups with the dosages of 20, 80, 320 mg/kg/day Allisartan respectively and a solvent control group. There were 14 males and 14 females in each group. During the whole test period, the behavior, activity, appearance, sign and the like of rats were observed every day. The examinations of hematology, hemagglutination, blood biochemistry and pathology were done for rats on the $26^{th}$ week after administration and at the end of six-week recovery after withdrawing the drugs. The result showed that there was no abnormal in the weights, feeding, hematology, blood biochemistry and pathology of rats, and the use of high dosage of Allisartan had quite good safety.

4. Safety of Long-Term Administration to Beagle Dogs

32 Beagle dogs were about six-month old with the weight of 6-7 kg each. Half of them were male, and half were female. They were randomly divided into 4 groups according to weight, eight per group. Allisartan was administered by gavage for 13 weeks. There were three groups with dosages of 20, 100, 500 mg/kg/day respectively and a solvent control group. The result showed that sign, appearance, behavior, activity, shape of feces and feeding in the groups with dosages of 20, 100, 500 mg/kg/day were normal. The weight and the weight gain were similar to those of the control group without statistical difference. The results of hematology, blood biochemistry, electrocardiogram, body temperature and urine examinations showed that each examination index was is similar to that of the control group, which fluctuated in the range of normal values.

Histopathology examination, in general or under microscope, both showed there was no drug correlated lesions in heart, lung, liver, spleen, kidney and the like, and there was no significant abnormal in other organs or tissues.

Example 4

The Preparation of Allisartan Tablets
Formulation:
Allisartan 5 g
Plasdone K-29/32 10 g
Polyplasdone XL(A) 26 g
Microcrystalline cellulose 10 g
Lactose 10 g
Polyplasdone XL(B) 3 g
Sodium stearyl fumarate 0.5 g
Preparation:
The drug and plasdone were dissolved in the mixture of proper amount of acetone and ethanol (v/v 1:1). Polyplasdone XL(A) was added into fluidized bed. The prepared solution was sprayed by spray gun in the form of top-spraying into the fluidized bed for granulation. After drying, the dried material and other materials were well-mixed, then tabletting. The average weight of the tablet was 250 mg. The dissolution measured was 96.7% at the time of 45 minutes.

Example 5

The Preparation of Allisartan Capsules
Formulation:
Allisartan 5 g
Microcrystalline cellulose 20 g
Lactose 20 g
Sodium carboxymethyl starch 5 g
Magnesium stearate 1 g
Polyplasdone proper amount
Preparation:
The drug and lactose were mixed, grinded, and passed through 80-100 mesh sieve. The previously grinded microcrystalline cellulose which passed through 80 mesh sieve and sodium carboxymethyl starch were added into ethanol solution containing 5%-20% of PVPK30 to prepare soft materials. 12-14 mesh particles were prepared by rocking granulating machine. Dried at the temperature of 50-90° C., the moisture of particles were controlled below 3%. Well-mixed, the particles were taken into the No. 1 capsule to obtain the product. The dissolution measured was 95.6% at the time of 45 minutes.

Example 6

The Preparation of Allisartan Potassium Capsules
Formulation:
Allisartan potassium 15 g
Microcrystalline cellulose 17 g
Lactose 15 g
Sodium carboxymethyl starch 2 g
Magnesium stearate 1 g
Ethanol solution with 10% Polyplasdone (PVPK30) proper amount
Preparation:
The drug and lactose were mixed, grinded, and passed through 80 mesh sieve. The previously grinded microcrystalline cellulose with 80 which passed through mesh sieve and sodium carboxymethyl starch were added into the proper amount of ethanol solution containing PVPK30 to prepare soft materials. The particles were prepared by rocking granulating machine. Dried at the temperature of 50-60° C., the moisture of particles were controlled below 3%. Well-mixed, the particles were taken into the No. 1 capsule to obtain the product. The dissolution measured was 95.5% at the time of 45 minutes.

Example 7

The Preparation of Allisartan Potassium Tablets
Formulation:
Allisartan potassium 5 g
Plasdone K-29/32 5 g
Microcrystalline cellulose 20 g
Lactose 20 g
Polyplasdone 4 g
Magnesium stearate 4 g
Preparation:
The drug and Plasdone K-29/32 were dissolved in a proper amount of methanol. The spray-dried sample was well-mixed with other materials, then tabletting. The dissolution measured was 95.5% at the time of 45 minutes.

Example 8

Phase I Clinical Trial of Allisartan and its Results

Voluntary healthy subjects were 19-45 year old. They entered into the clinical trial ward before the date of the trial, ate light diet at night then fasted for 10 h without inhibiting water overnight. Allisartan tablets were administered by oral administration. The subjects were fasted on next morning, with the dosages from low to high (20 mg, 50 mg, 90 mg, 150 mg, 250 mg, 400 mg). The next dosage can be taken only after the observation of the effect of the last dosage. Heart rate, rhythm, respiration, blood pressure and body temperature were observed at different time before and after the trial. The examination of hematology (red blood cell count, hemoglobin content, hematocrit, leukocyte count, platelet count, clotting time and bleeding time), routine urine test, routine stool test, occult blood test, liver function (ALT), renal function (BUN, Cr) and ECG were observed at different time before and after the trial. Adverse reaction of subjects were observed and recorded strictly.

The results of the trial showed that it was very safe for healthy subjects to take Allisartan (20-40 mg) by single oral administration. They had no adverse reaction and serious adverse reaction events.

All documents referred to throughout this application are hereby incorporated in their entireties by reference herein, as if each of them is individually incorporated. Further, it would be appreciated that, in light of the above described teaching of the invention, the skilled in the art could make various changes or modifications to the invention, and these equivalents would still be within the scope of the invention defined by the appended claims of the application.

The invention claimed is:
1. A method for the treatment of the damage of a target organ caused by hypertension, comprising administering to a subject in need thereof a compound of formula (I) or a pharmaceutically acceptable salt thereof

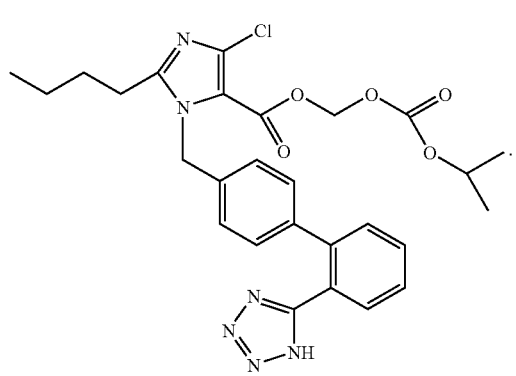

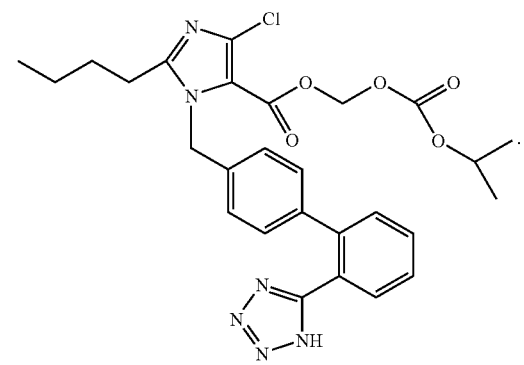

2. The method according to claim 1, wherein the compound of formula (I) or the pharmaceutically acceptable salt thereof is administered in the dosage of about 0.1-about 50 mg/kg/day.

3. The method according to claim 1, wherein the compound of formula (I) or the pharmaceutically acceptable salt thereof is administered in the dosage of about 0.5-about 20 mg/kg/day.

4. The method according to claim 1, wherein said damage of a target organ comprises the damage of heart, brain, kidney or blood vessel caused by hypertension.

5. The method according to claim 4, wherein said damage of a target organ comprises left ventricular hypertrophy, stroke, renal cortex atrophy or aorta thickening.

6. The method according to claim 1, wherein the compound of formula (I) or the pharmaceutically acceptable salt thereof is formulated in a medicament, wherein said medicament comprises about 20 mg-1000 mg of the compound of formula (I) or a pharmaceutically acceptable salt thereof, and a pharmaceutically acceptable carrier.

7. The method according to claim 1, wherein the compound of formula (I) or the pharmaceutically acceptable salt thereof is formulated in a medicament, wherein said medicament comprises about 50-about 500 mg of the compound of formula (I) or a pharmaceutically acceptable salt thereof, and a pharmaceutically acceptable carrier.

8. The method according to claim 1, wherein the dosage form of said medicament is an oral dosage form, injection, formulation for sublingual administration, or patch, preferably comprises tablet, capsule, granule, pill, or suspension.

9. A method for the treatment of the damage of a target organ caused by hypertension, comprising administering to a subject in need thereof a composition comprising the compound of formula (I) or a pharmaceutically acceptable salt thereof 10. The method according to claim 9, wherein the content of the compound of formula (I) or the pharmaceutically acceptable salt thereof in the composition is about 20 mg-about 1000 mg.

11. A pharmaceutical composition for oral or sublingual administration, which contains about 50 mg-about 1000 mg of a compound of formula (I) or a pharmaceutically acceptable salt thereof, and a pharmaceutically acceptable carrier

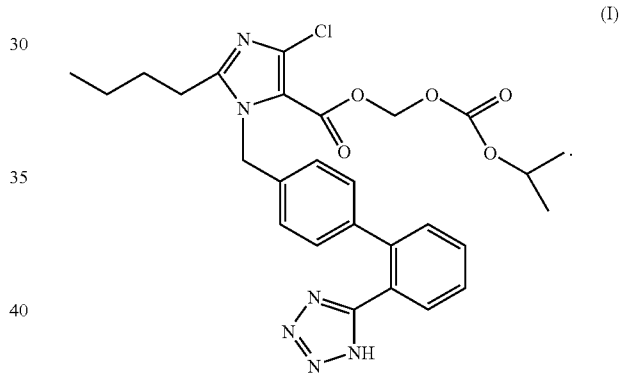

12. The pharmaceutical composition according to the claim 11, wherein the content of the compound of formula (I) or the pharmaceutically acceptable salt thereof in said composition is about 100 mg, about 200 mg, about 300 mg, about 400 mg, about 500 mg or about 1000 mg.

* * * * *